United States Patent [19]
Brautigam et al.

[11] Patent Number: 4,964,961
[45] Date of Patent: Oct. 23, 1990

[54] ELUTION METHOD AND DEVICE

[75] Inventors: Kathe L. Brautigam, St. Petersburg; William W. Gorman, Jr., Treasure Island, both of Fla.

[73] Assignee: E-C Apparatus Corporation, St. Petersburg, Fla.

[21] Appl. No.: 388,494

[22] Filed: Aug. 2, 1989

[51] Int. Cl.$^5$ ............................ C25B 7/00; C07K 3/14
[52] U.S. Cl. ............................... 204/182.3; 204/180.1; 204/182.8; 204/299 R; 204/301
[58] Field of Search ............... 204/180.1, 182.3, 182.8, 204/299 R, 301

[56] References Cited

U.S. PATENT DOCUMENTS

| | | | |
|---|---|---|---|
| 3,579,433 | 5/1971 | Dahlgren | 204/182.8 |
| 3,640,813 | 2/1972 | Nerenberg | 204/182.8 |
| 3,791,950 | 2/1974 | Allington | 204/182.8 |
| 4,545,888 | 10/1985 | Walsh | 204/301 |
| 4,552,640 | 11/1985 | Kartenbeck | 204/301 |
| 4,608,147 | 8/1986 | Clad | 204/301 |
| 4,699,706 | 10/1987 | Burd et al. | 204/301 |

OTHER PUBLICATIONS

Lewis et al., "Preparative Methods for Disk Electrophoresis With Special Reference to the Isolation of Pituitary Harmones", Anal. Biochemistry 6(1963), pp. 303-315.

Primary Examiner—T. Tung
Assistant Examiner—David G. Ryser
Attorney, Agent, or Firm—Bernard, Rothwell & Brown

[57] ABSTRACT

The present invention is directed to an apparatus for electro elution of components separated by preparative electrophoresis on a gel comprising a tapered tube divided by a porous disc into an upper section which is open at the top of the tapered tube and a lower section which is closable by a removable cap. The apparatus also contains a dialysis membrane of substantially the same diameter as the removable cap and affixed to the removable cap such that the dialysis membrane is sealed against the end of the tapered tube when the removable cap encloses the lower section of the tapered tube. Following electro elution, the open upper section of the tapered tube can be sealed and the desired substance is withdrawn through the cap and dialysis membrane which encloses the lower end of the tube. An auxiliary funnel can be affixed to the open upper end of the tube to increase the capacity of the system.

17 Claims, 3 Drawing Sheets

ELUTION METHOD AND DEVICE

FIELD OF THE INVENTION

This invention relates to an apparatus and method of recovery by electrophoresis. Specifically, the invention relates to an elution device for recovering proteins, nucleic acids and other substances separated by preparative electrophoresis through the use of electro elution.

BACKGROUND OF THE INVENTION

Electrophoresis of large charged molecules, such as nucleic acids, deoxyribonucleic acid (DNA) fragments, or proteins has been an established laboratory method for approximately 25 years. In its most common form, an electric field is imposed between opposite ends of a thin slab of gel. A sample, containing a mixture of various charged molecules is introduced into one end of the gel. The electric field causes the molecules to migrate to the opposite end of the gel. The velocity at which each substance of interest migrates is dependent upon its mobility, a characteristic determined by the length of the substance, shape, and other characteristics. Molecules having similar mobility will migrate as a band at a given velocity. With time, the sample will be separated into distinct bands, each composed of like molecules.

By means of staining or radioactive tagging, the various nucleic acids or proteins of interest can be located and identified. As described above, electrophoresis is a simple and sensitive analytical technique. The recovery of the nucleic acids or proteins from the gel following electrophoresis has historically been difficult. Several methods have been tried for recovering these substances.

For example, one method is the crush and soak method which involves excising the gel material containing the substance to be recovered from the gel slab and grinding or crushing the gel material. The crushed gel material then is soaked in a salt solution for long periods of time. This extracts the desired protein or nucleic acid from the gel. The substance then is ethanol precipitated from the salt solution. This process is quite slow and is not efficient for most purposes.

Another method for recovering substances from gel material known in the art is the melting agarose/chemical extraction method whereby the gel material containing the nucleic acid or protein to be recovered is excised from the gel slab and is melted at about 65° C. Phenol extraction is followed by organic chemical purification. The recovery efficiency by this method is relatively low and the purification procedures are long and labor intensive.

The blitz blotting method of recovery entails placing the entire gel slab in contact against a sheet of DEAE cellulose paper, which is known for its ability to bind DNA fragments. This sandwich then is immersed in a buffer solution and by electrophoretic means, all the bands are transferred from the gel to the DEAE paper. This method has a relatively high recovery efficiency, but the apparatus is costly and cumbersome. Another method using DEAE involves cutting slots in the gel immediately downstream of each of the bands. DEAE paper is inserted into the slots and by means of electrophoresis, the bands are driven into the DEAE paper. This method is extremely technique dependent. Cutting the slot deforms the electric field which causes varying portions of the band to be driven around the slot.

The gel decomposition/glass beads method of recovery requires decomposing the gel material containing the material of interest by chemical means. The resulting mixture, in a buffer, is poured over glass beads which are removed and washed. The nucleic acid or protein is eluted from the glass beads with a salt solution. The method results in fair recovery efficiency with large molecules, but buffer conditions are very critical.

U.S. Pat. No. 4,552,640, issued to Kartenbeck (1985), describes an electrophoretic apparatus for the quantitative elution of proteins or polypeptides from a gel which includes an upper chamber for holding a buffer solution containing the gel from which the proteins or polypeptides are to be eluted. An upper electrode is provided in the upper chamber. A lower chamber for holding a buffer solution is disposed beneath the upper chamber and includes a lower electrode. A septum separates the upper chamber from the lower chamber. A connecting passage in the septum connects the upper and lower chambers. A collecting capsule for the proteins or polypeptides is formed from a dialysis membrane material and is disposed at the end of the connecting passage in the lower chamber. The capsule is adapted to be suspended in the buffer solution which is to be held in the lower chamber.

The Kartenbeck apparatus suffers from several disadvantages. The dialysis membrane, due to its relatively large surface area, can adversely adsorb the very material sought to be recovered. Also, the relatively large volume of the lower chamber can cause undue dilution of the sample.

U.S. Pat. No. 4,545,888, issued to Walsh (1985), describes an apparatus for the recovery of nucleic acids and other substances which consists of a plurality of transfer chambers suitably supported in a vessel for containing an aqueous buffer solution, a plurality of filter discs for support of a layer of DEAE cellulose resin in the bottom of the transfer chambers, a plurality of negative electrodes, a positive electrode for placement in the buffer which will surround the plurality of transfer chambers, and a power supply. A gel slab containing nucleic acids is placed into the transfer chambers. When an electric current is passed through the chambers, the nucleic acids migrate to the positive electrode. On passing through the DEAE, the nucleic acids are brought into intimate contact with the DEAE resin and are bound to the surface of the DEAE resin. The nucleic acids are recovered by established elution procedures. This process requires an extra elution step and thus, is not efficient.

U.S. Pat. No. 4,699,706, issued to Burd (1987), also describes an electrophoretic method and apparatus for extraction of species from electrophoresis media. This method involves placing a separation medium in a tube closed at one end by a retaining material such as a glass frit, and sealing the closed end of the tube against the mouth of a receiving cup which has a semipermeable membrane for its bottom. The tube with receiving cup attached is inserted in a tube electrophoresis cell such as those commonly used in analytical laboratories. As current passes through the tube, the molecular species migrates from the separation medium to pass through the retaining frit and collect on the membrane for subsequent recovery. The structure used for recovery in this method is complex since the dialysis membrane must be held in place by a retaining ring, a gasket and internal shoulders. No provision is made for capping the column to hydraulically isolate the sample collected in the sample cup. Removal of the sample cup may lead to the disruption of the collected sample because of leakage through the frit or due to excess fluid in the sleeve holding the cup. Further, the recovery is inefficient since the dialysis membrane is smaller than the diameter of the frit.

There is a need in the art for a simple, convenient, inexpensive apparatus and method for elution of proteins, enzymes or nucleic acids from gels used in electrophoresis.

SUMMARY OF THE INVENTION

The present invention is directed to an apparatus for electro elution (also known as elution electrophoresis) of components separated by preparative electrophoresis on a gel, comprising:

(a) a tapered tube divided by a porous disc into an open upper section and a lower section which is closable by a removable cap; and (b) a dialysis membrane of substantially the same diameter as the removable cap and affixed to the removable cap such that the dialysis membrane is sealed against the end of the tapered tube when the removable cap closes the lower section of the tapered tube.

In one embodiment an auxiliary funnel is attached to the top of the tapered tube in order to increase the gel fragment capacity of the system.

The invention also is directed to a method for performing electro elution upon a sample, comprising:

(A) providing an elution apparatus comprising:
(a) a tapered tube divided by a porous disc into an open upper section and a lower section which is closable by a removable cap; and
(b) a dialysis membrane of substantially the same diameter as the removable cap and affixed to the removable cap such that the dialysis membrane is sealed against the end of the tapered tube when the removable cap closes the lower section of the tapered tube;

(B) placing the sample within the upper section of the tapered tube; and (C) applying an electric current through the sample to cause migration of a desired substance from the sample, through the porous disc and into the lower section of the tapered tube.

DETAILED DESCRIPTION OF THE PREFERRED EMBODIMENT

Figure 1:
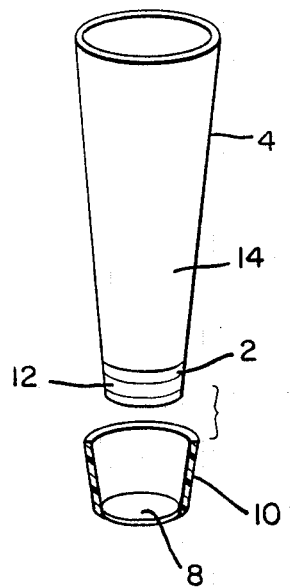
FIG. 1 is an exploded view of an embodiment of an apparatus for the recovery of proteins or nucleic acids from a gel.

The apparatus of the present invention is useful for electro elution of components separated by preparative electrophoresis on a gel. One embodiment of the apparatus is shown in FIG. 1. The tapered tube 4 has tapered sides such that the diameter of the tube decreases towards the bottom of the tube. The tube is divided by a porous disc (frit) 2 into two sections, an upper section 14 and a lower section 12. A cap 10 is used to enclose the bottom of the tube 4. The cap contains a dialysis membrane 8 of substantially the same diameter as the removable cap and which is affixed to the removable cap such that the dialysis membrane is sealed against the end of the tapered tube when the removable cap encloses the lower section of the tapered tube. The dialysis membrane preferably is attached to the outer bottom surface of the cap. When the cap is placed on the tapered tube, an eluate section is formed between the porous disc and the dialysis membrane. This eluate section will contain the molecular species to be recovered when the elution device is used.

The tapered tube generally will be made of plastic material which does not bind up nucleic acids or proteins or other substances which are to be recovered from electrophoresis gels. Also, the plastic material should not denature the biological materials subject to elution and should be fluid impermeable. Examples of useful plastic materials include polypropylene or polyethylene, with polypropylene being preferred.

The porous disc, likewise, is made of a plastic material which does not bind up nucleic acids, proteins or other substances which are to be recovered and does not denature biological materials. The plastic material can, for example, be polypropylene or polyethylene. The porous disc preferably is formed from polypropylene. The size of the disc will depend on the desired size of the lower and upper sections of the tapered tube. If the lower section is to be relatively large, the disc accordingly will be large so as to fit higher up in the tapered tube. Similarly, if it is desired that the lower section be small, the disc will be smaller to fit farther down the tube. The size of the lower section or eluate section formed when the tube is capped is varied depending on the substance or molecules to be recovered. When DNA fragments are to be recovered, it has been found that the smallest possible eluate section is preferable. Other molecules may be better recovered in a larger eluate section.

In one embodiment, the porous disc is inserted into the tube by mechanical means and forms a mechanical seal with the inner surface of the tapered tube from the force of placing the disc into the tube.

The removable cap may be made of any material to which the dialysis membrane can be affixed. One material found to be particularly useful is acrylic. Since acrylic has a charge on its surface that can attract and bind materials such that the yield of the elution is greatly reduced, the dialysis membrane is affixed to the removable cap such that the dialysis membrane is sealed against the end of the tapered tube when the removable cap encloses the lower section of the tapered tube to form the eluate section. This prevents the materials within the tube from coming in contact with the acrylic material. Rather, the materials within the tube only come in contact with the sides of the tube, the porous disc and the dialysis membrane.

The dialysis membrane generally is of a cellulose material which retains molecules and allows liquid to freely flow therethrough. The pore size of the membrane is selected with the material to be recovered in mind. The specific dialysis membrane optimal for use in recovering a specific molecular specie for a particular purpose will be known to persons of ordinary skill in the art. The membrane is affixed to the removable cap by an adhesive or glue. The diameter of the dialysis membrane preferably will be substantially the same diameter as the porous disc. This leads to greater recovery of the substances (especially in the case of DNA) to be recovered from the electrophoresis gels.

The tube is sized to accommodate the pieces of gel or other support medium which contains the species to be extracted and collected. The support medium generally is gel slices containing proteins, enzymes or nucleic acids which previously have been electrophoretically isolated from a mixture of such molecules. The tube is sized such that it can replace electrophoresis tubes in a common laboratory tube electrophoresis cell.

Figure 2:
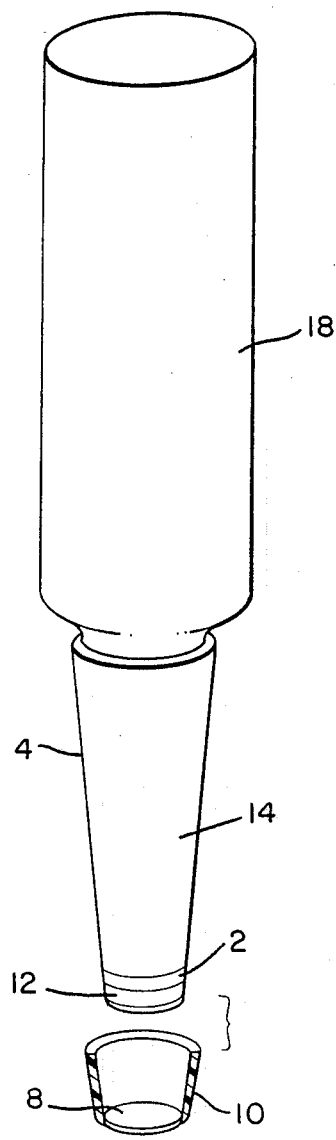
FIG. 2 illustrates the apparatus of FIG. 1 in combination with an auxiliary funnel.

The useful capacity of the elution tube can be increased by the attachment of an auxiliary funnel as is seen in FIG. 2. The funnel 18 is pressure-fit onto the open, upper end of the tapered tube 4 and remains in place during electro elution. Funnels of various sizes can be provided to meet the particular needs of the user.

Figure 3:
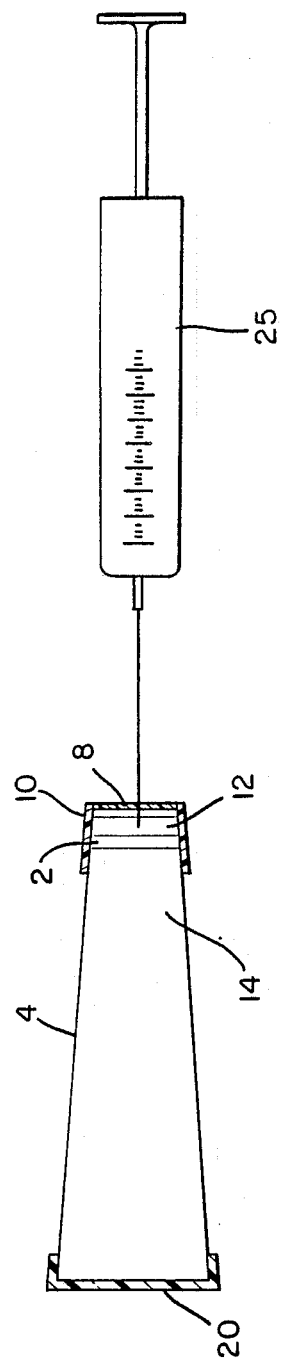
FIG. 3 illustrates the removal of a sample following electro elution.

FIG. 3 illustrates a preferred method for removing a sample following electro elution. Auxiliary funnel 18 has been removed and replaced by a fluid-tight plastic cap 20. The tapered tube 4 is placed on its side and the cap 10 and membrane 8 are pierced with a syringe. The syringe is used to draw off the sample which has collected within the eluate section (lower chamber) 12.

The apparatus of the present invention is used for electro elution in a manner which is known to those of ordinary skill in that art. In one embodiment, the tube and the cap are separate at first while buffer is added to each. Generally, the buffer added to the tube flows through the porous disc and drips out the end of the tube. The cap also is filled with buffer and the tube and cap then are pushed together. This procedure is preferable since it alleviates air bubbles in the tube which can result in only partial elution of the sample or can cause the sample to elute more slowly. The support material from which the nucleic acids, enzymes or proteins are to be separated, such as gel material, is placed into the upper section of the tube. The tube and cap combination then is placed in an inner tank of the electrophoresis cell and buffer is poured into the upper chamber of the inner tank. The buffer should be added at least until the electrodes of the cell are covered. The inner tank then is placed in an outer tank also containing buffer. The buffer of the inner tank generally will only be in contact with the buffer of the outer tank through the tapered tube elution device of the present invention. This allows the molecules of interest to elute through the porous disc of the tube into the eluate section. Electric current is supplied from the electrophoresis cell causing electrophoretic migration of molecular species from the gel material past the porous disc into the cap containing the dialysis membrane, from where the desired material can be recovered.

The following example further illustrates the process of this invention, but is not meant to limit the scope of the invention in any way.

EXAMPLE

Preparative 1% agarose gel containing Lambda DNA Hind (III) digest was separated, and the fragments excised, to be eluted using the apparatus of the present invention as follows:

The elution columns are labeled with a grease pencil and a moderate wiping of petroleum jelly or high vacuum silicone grease is placed on the tubes where the membrane cap will seat. Approximately 2 ml. of buffer is added to an elution tube and permitted to drip through the porous filter until approximately 0.5 ml. of buffer remains. The membrane cap is filled with buffer and placed on the tube so that no air bubbles are present in the 200 $\mu$l +/- 100 $\mu$l eluate chamber.

The elution tube with membrane cap in place is inserted into the inner buffer tank making a tight seal. Six elution tubes are similarly positioned within each elution column and small polyethylene plugs are placed in the gel column grommets.

One thousand ml. of buffer is added to the outer, lower buffer tank. The upper, inner buffer tank with columns in position is inserted into the lower buffer tank and the tubes are checked to insure that air bubbles are not trapped on the membrane of the cap. The upper buffer tank is filled with buffer making sure that both the electrodes and elution tubes are completely submerged with no air pockets remaining at the top of the tubes. Gel fragments then are added to appropriate columns.

The electrodes are connected to a suitable power source so that the upper, inner chamber is the cathode (−) and the bottom, outer tank is the anode (+). The system is run at constant current (2 mA/column) overnight.

Following electro elution, the upper reservoir is drained by the removal of a polyethylene plug. Using a syringe, approximately 500 $\mu$l of buffer is removed from the tapered elution tube. The elution tube is capped and the dialysis membrane is punctured with a needle which is used to draw up eluate. The eluates are recovered and extracted in accordance with standard laboratory procedures.

We claim:

1. A method for performing electro elution upon a sample, comprising:
 (A) providing an elution apparatus comprising:
  (a) a tapered tube having a decreased diameter toward an end of the tapered tube and being divided by a porous disc into an open upper section and a lower section which is closable by a removable cap; and
  (b) a dialysis membrane of substantially the same diameter as the removable cap and affixed to the removable cap such that the dialysis membrane is sealed against the end of the tapered tube when the removable cap closes the lower section of the tapered tube;
 (B) placing the sample within the upper section of the tapered tube; and
 (C) applying an electric current through the sample to cause migration of a desired substance from the sample, through the porous disc and into the lower section of the tapered tube.

2. The method of claim 1 further comprising the steps of
 (D) sealing the upper section of the tapered tube; and
 (E) removing the desired substance through the removable cap.

3. The method of claim 2 wherein the removing step is performed with a syringe.

4. A method for performing electro elution upon a sample, comprising:
 (A) providing an elution apparatus comprising:
  (a) a tapered tube having a decreased diameter toward an end of the tapered tube and being divided by a porous disc into an open upper section and a lower section which is closable by a removable cap;
  (b) a dialysis membrane of substantially the same diameter as the removable cap and affixed to the removable cap such that the dialysis membrane is sealed against the end of the tapered tube when the removable cap closes the lower section of the tapered tube; and (c) an auxiliary funnel in fluid connection with the open upper section of the tapered tube;

(B) placing the sample within the auxiliary funnel; and (C) applying an electric current through the sample to cause migration of a desired substance from the sample, through the porous disc and into the lower section of the tapered tube.

5. The method of claim 4 further comprising the steps of (D) sealing the upper section of the tapered tube; and (E) removing the desired substance through the removable cap.

6. The method of claim 5 wherein the removing step is performed with a syringe.

7. An apparatus for electro elution of components separated by analytical electrophoresis on a gel comprising:

(a) a tapered tube having a decreased diameter toward an end of the tapered tube and being divided by a porous disc into an open upper section and a lower section which is closable by a removable cap; and (b) a dialysis membrane of substantially the same diameter as the removable cap and affixed to the removable cap such that the dialysis membrane is sealed against the end of the tapered tube when the removable cap closes the lower section of the tapered tube.

8. The apparatus of claim 7 wherein the porous disc is placed int he tapered tube so as to form a mechanical seal between the porous disc and an inner surface of the tapered tube.

9. The apparatus of claim 8 wherein the diameter of the dialysis membrane is substantially the same as the diameter of the porous disc.

10. The apparatus of claim 8 wherein the volume of the lower section is determined by the diameter of the porous disc.

11. The apparatus of claim 7 wherein the porous disc is plastic.

12. The apparatus of claim 11 wherein the porous disc is polypropylene.

13. The apparatus of claim 7 wherein the tapered tube is plastic.

14. The apparatus of claim 13 wherein the tapered tube is polypropylene.

15. The apparatus of claim 7 wherein the removable cap is acrylic.

16. The apparatus of claim 7 further comprising an auxiliary funnel in fluid connection with the open upper section of the tapered tube.

17. The apparatus of claim 7 wherein the removable cap is tapered and has the same taper as the tapered tube.

* * * * *